United States Patent
Nishimori et al.

(10) Patent No.: US 10,982,094 B2
(45) Date of Patent: Apr. 20, 2021

(54) OPTICAL MATERIAL COMPOSITION

(71) Applicant: MITSUBISHI GAS CHEMICAL COMPANY, INC., Tokyo (JP)

(72) Inventors: Yoshihiko Nishimori, Tokyo (JP); Yosuke Imagawa, Tokyo (JP); Kouhei Takemura, Tokyo (JP); Hiroshi Horikoshi, Tokyo (JP); Yoshiaki Yamamoto, Tokyo (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 51 days.

(21) Appl. No.: 16/483,542

(22) PCT Filed: Feb. 6, 2018

(86) PCT No.: PCT/JP2018/004014
§ 371 (c)(1),
(2) Date: Aug. 5, 2019

(87) PCT Pub. No.: WO2018/150950
PCT Pub. Date: Aug. 23, 2018

(65) Prior Publication Data
US 2020/0024450 A1   Jan. 23, 2020

(30) Foreign Application Priority Data

Feb. 17, 2017   (JP) .............................. JP2017-027502

(51) Int. Cl.
| | | |
|---|---|---|
| *C08L 81/02* | (2006.01) | |
| *C08G 75/08* | (2006.01) | |
| *C08K 3/06* | (2006.01) | |
| *G02B 1/04* | (2006.01) | |
| *C07D 331/02* | (2006.01) | |

(52) U.S. Cl.
CPC ............ *C08L 81/02* (2013.01); *C07D 331/02* (2013.01); *C08G 75/08* (2013.01); *C08K 3/06* (2013.01); *G02B 1/04* (2013.01); *G02B 1/041* (2013.01); *C08L 2201/10* (2013.01)

(58) Field of Classification Search
CPC ... C08L 81/02; C08L 2201/10; C07D 331/02; C08G 75/08; C08K 3/06; G02B 1/04; G02B 1/041
See application file for complete search history.

(56) References Cited

U.S. PATENT DOCUMENTS

| | | |
|---|---|---|
| 5,807,975 A | 9/1998 | Amagai et al. |
| 5,945,504 A | 8/1999 | Amagai et al. |
| 6,117,923 A | 9/2000 | Amagai et al. |
| 6,180,753 B1 | 1/2001 | Amagai et al. |
| 6,531,532 B1 | 3/2003 | Yoshimura et al. |
| 2004/0254258 A1* | 12/2004 | Horikoshi ............... G02B 1/04 523/102 |
| 2018/0127549 A1 | 5/2018 | Imagawa et al. |
| 2018/0265638 A1 | 9/2018 | Namiki et al. |
| 2020/0024450 A1 | 1/2020 | Nishimori et al. |

FOREIGN PATENT DOCUMENTS

| | | |
|---|---|---|
| JP | 9-71580 | 3/1997 |
| JP | 9-255781 | 9/1997 |
| JP | 10-298287 | 11/1998 |
| JP | 2000-128988 | 5/2000 |
| JP | 2001-2933 | 1/2001 |
| JP | 2001-98072 | 4/2001 |
| JP | 2010-242093 | 10/2010 |
| JP | 2011-231185 | 11/2011 |
| WO | 2012/112015 A2 | 8/2012 |
| WO | 2016/204080 | 12/2016 |
| WO | 2017/098798 A1 | 6/2017 |
| WO | 2018/150950 A1 | 8/2018 |

OTHER PUBLICATIONS

Official Communication issued in International Patent Application No. PCT/JP2018/004014, dated May 15, 2018.
Supplementary European Search Report dated Feb. 4, 2020 in European Application EP 18754376.4.

* cited by examiner

*Primary Examiner* — Shane Fang
(74) *Attorney, Agent, or Firm* — Greenblum & Bernstein, P.L.C.

(57) ABSTRACT

Provided is an optical material composition which makes it possible to design an optical material exhibiting a broad range of properties. This optical material composition contains a compound (A) represented by formula (1), 1,2,3,5, 6-pentathiepane (b), and if necessary, a compound (B) represented by formula (2). The content of the compound (B) constitutes 0-30 mass % of the total mass of the composition:

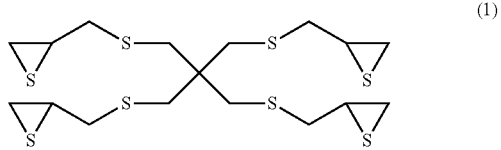

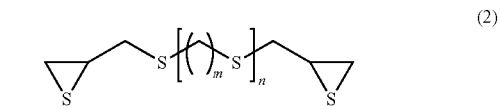

(In the formula, n m represents an integer which is 0-4, and n represents an integer which is 0-2).

13 Claims, No Drawings

OPTICAL MATERIAL COMPOSITION

TECHNICAL FIELD

The present invention relates to an optical material composition for use in optical components including plastic lenses, prisms, optical fibers, information recording substrates, filters and adhesives, particularly optical lenses such as plastic lenses for use in spectacles.

BACKGROUND ART

The major performance of plastic materials required for optical materials, particularly spectacle lenses, is optical performance including heat resistance, low specific gravity, high transparency and low yellowness index, as well as high refractive index and high Abbe's number. In recent years, in an attempt to achieve high refractive index and high Abbe's number, there has been proposed a polymerizable composition for optical materials, which comprises a polyepisulfide compound (Patent Documents 1 to 3).

Moreover, optical lenses such as spectacle lenses are treated by dyeing, hard coating and antireflection coating with the aim of improved designability, durability and optical properties. During the step of such treatment, optical materials are exposed to high temperature and may experience problems due to thermal deformation. For this reason, there is a need to improve the heat resistance of optical materials. With the aim of ensuring high refractive index and/or improved color tone stability in optical materials, various comonomers are added to optical material compositions.

However, upon addition of comonomers, optical materials obtained after polymerization tend to impair their heat resistance due to reduced crosslinking density. Thus, in terms of heat resistance, there is a limit in the amount of comonomers to be added, which in turn causes a problem in that optical materials are limited in the range of their properties which can be improved. For this reason, there is a demand for improving heat resistance, which serves as a basis, to thereby increase the possible amount of comonomers to be added, thus resulting in an optical material composition which enables the design of an optical material having a wide range of physical properties.

PRIOR ART DOCUMENTS

Patent Documents

Patent Document 1: JP H10-298287 A
Patent Document 2: JP 2001-002933 A
Patent Document 3: JP 2010-242093 A

SUMMARY OF THE INVENTION

Problem to be Solved by the Invention

There is a demand for the provision of an optical material composition which enables the design of an optical material with improved heat resistance and having a wide range of physical properties.

Means to Solve the Problem

The inventors of the present invention have found that a certain composition comprising a compound represented by the following formula (1) enables the design of an optical material having a wide range of physical properties. Namely, the present invention is as follows.

[1] An optical material composition, which comprises a compound (A) represented by the following formula (1), 1,2,3,5,6-pentathiepane (b), and optionally a compound (B) represented by the following formula (2), wherein the content of the compound (B) is 0% to 30% by mass relative to the total mass of the composition:

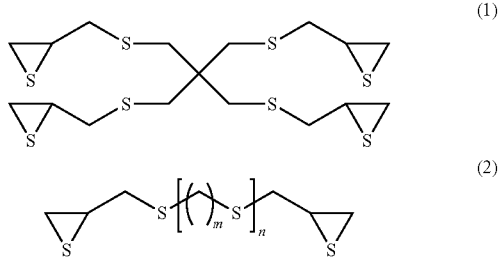

(wherein m represents an integer of 0 to 4, and n represents an integer of 0 to 2).

[2] The optical material composition according to [1] above, wherein the content of the compound (A) is 20% to 80% by mass relative to the total mass of the composition.

[3] The composition according to [1] or [2] above, which further comprises a polythiol (a).

[4] The composition according to [3] above, wherein the polythiol (a) is at least one selected from 1,2,6,7-tetramercapto-4-thiaheptane, methanedithiol, (sulfanylmethyldisulfanyl)methanethiol, bis(2-mercaptoethyl)sulfide, 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, tetramercaptopentaerythritol, 1,3-bis(mercaptomethyl)benzene, 1,4-bis(mercaptomethyl)benzene, and thiiranemethanethiol.

[5] The composition according to any one of [1] to [4] above, which further comprises sulfur.

[6] The composition according to any one of [1] to [5] above, wherein the mass ratio of the compound (A) to the compound (B) is 45:55 to 100:0.

[7] The composition according to any one of [1] to [6] above, wherein the mass ratio of the compound (A) to 1,2,3,5,6-pentathiepane (b) is 25:75 to 95:5.

[8] The composition according to any one of [1] to [7] above, wherein the content of 1,2,3,5,6-pentathiepane (b) is 5% to 70% by mass relative to the total mass of the composition.

[9] The composition according to any one of [1] to [8] above, which comprises:

| | |
|---|---|
| the compound (A) | 20% to 80% by mass; |
| 1,2,3,5,6-pentathiepane (b) | 5% to 70% by mass; |
| the compound (B) | 0% to 30% by mass; |
| the polythiol (a) | 0% to 10% by mass; and |
| sulfur | 0% to 25% by mass | relative to the total mass of the composition.

[9a] The composition according to any one of [1] to [9] above, which comprises:

| | |
|---|---|
| the compound (A) | 20% to 80% by mass; |
| 1,2,3,5,6-pentathiepane (b) | 5% to 70% by mass; |
| the compound (B) | 0% to 30% by mass; |
| the polythiol (a) | 0% to 10% by mass; |
| sulfur | 0% to 25% by mass; |
| a polymerization catalyst | 0% to 10% by mass; and |
| a polymerization regulator | 0% to 5% by mass | relative to the total mass of the composition.

[10] The composition according to any one of [1] to [9] and [9a] above, wherein the composition when cured has a refractive index of 1.75 or higher for e-ray at 25° C.

[11] An optical material cured from the composition according to any one of [1] to [10] and [9a] above.

[12] An optical lens comprising the optical material according to [11] above.

Effects of the Invention

The optical material composition of the present invention has one or more of the following effects.
(1) As a result of using the optical material composition of the present invention, heat resistance is improved and the possible amount of comonomers to be added is increased, thus enabling the design of an optical material having a wide range of physical properties.
(2) It is possible to obtain an optical material with good heat resistance and high refractive index.

DESCRIPTION OF EMBODIMENTS

The present invention will be further described in more detail below by way of the following embodiments and illustrations, although the present invention is not limited to the following embodiments and illustrations and can be implemented with modifications as appropriate without departing from the spirit of the present invention.

One embodiment of the present invention is directed to an optical material composition, which comprises a compound (A) represented by the following formula (1), 1,2,3,5,6-pentathiepane (b), and optionally a compound (B) represented by the following formula (2), wherein the content of the compound (B) is 0% to 30% by mass relative to the total mass of the composition:

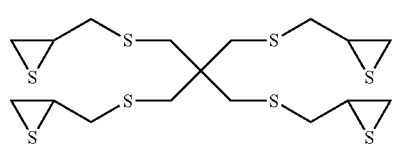

(wherein m represents an integer of 0 to 4, and n represents an integer of 0 to 2).

A detailed explanation will be given below of each constituent element.

[Compound (A)]

The compound (A) is a thioether compound having four thioepoxy groups, which is represented by the following formula (1), and has the effect of increasing the refractive index and heat resistance of the resulting optical material.

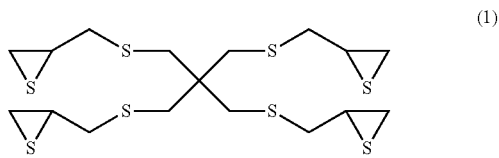 [SMILES: C(SCC(CSCC1CS1)(CSCC1CS1)CSCC1CS1)C1CS1]

This compound is available in any way and, for example, may be synthesized starting from tetramercaptopentaerythritol in accordance with the process described in JP H09-110979 A, which is preferred for use.

The ratio of the compound (A) in the optical material composition is 0.1% to 99.5% by mass, preferably 3% to 90% by mass, more preferably 5% to 90% by mass, even more preferably 10% to 90% by mass, still more preferably 20% to 90% by mass, particularly preferably 20% to 80% by mass, and most preferably 20% to 50% by mass, relative to the total mass of the composition. Within this range, it is possible to obtain a sufficient improving effect on heat resistance.

[Polythiol (a)]

The optical material composition may optionally comprise a polythiol (a). The polythiol (a) is a thiol compound having two or more mercapto groups per molecule. The polythiol (a) has the effect of improving the color tone of the resin obtained from the optical material composition of the present invention during heating.

The polythiol for use in the present invention is not limited in any way. However, specific examples which are preferred in terms of having a high improving effect on color tone include 1,2,6,7-tetramercapto-4-thiaheptane, methanedithiol, (sulfanylmethyldisulfanyl)methanethiol, bis(2-mercaptoethyl)sulfide, 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, tetramercaptopentaerythritol, 1,3-bis(mercaptomethyl)benzene, 1,4-bis(mercaptomethyl)benzene, and thiiranemethanethiol. Among them, bis(2-mercaptoethyl)sulfide and 1,2,6,7-tetramercapto-4-thiaheptane are particularly preferred, and 1,2,6,7-tetramercapto-4-thiaheptane is most preferred. For use in the present invention, these compounds may be commercially available or synthesized by any known process, and two or more of them may be used in combination. For use in the present invention, these compounds may be commercially available or synthesized by any known process, and two or more of them may be used in combination.

The ratio of the polythiol (a) in the optical material composition is preferably 0% to 25% by mass (e.g., 0.1% to 25% by mass), more preferably 0% to 20% by mass (e.g., 0.5% to 20% by mass), even more preferably 0% to 10% by mass (e.g., 0.5% to 10% by mass), and particularly preferably 0% to 5% by mass (e.g., 0.5% to 5% by mass), relative to the total mass of the composition. Within this range, it is possible to ensure a good balance between the stabilizing effect on color tone and heat resistance.

1,2,3,5,6-pentathiepane (b)

1,2,3,5,6-pentathiepane (b) is a compound represented by the following formula (b) and has the effect of improving the refractive index of the optical material (resin) obtained from the optical material composition of the present invention.

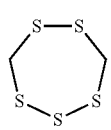

(b)

1,2,3,5,6-pentathiepane (b) is available in any way. It may be commercially available, may be collected or extracted from crude oil or naturally occurring products of animal or plant origin, or may be synthesized by any known process.

Examples of its synthesis process include the processes described in N. Takeda et al., Bull. Chem. Soc. Jpn., 68, 2757 (1995), F. Feher et al., Angew. Chem. Int. Ed., 7, 301 (1968), G. W. Kutney et al., Can. J. Chem, 58, 1233 (1980), etc.

The ratio of 1,2,3,5,6-pentathiepane (b) when used in the optical material composition is preferably 5% to 70% by mass, and more preferably 5% to 50% by mass, relative to the total mass of the composition. Within this range, it is possible to ensure not only improved refractive index, but also the transparency of the resulting optical material.

The mass ratio of the compound (A) to 1,2,3,5,6-pentathiepane (b) (i.e., compound (A): 1,2,3,5,6-pentathiepane (b)) is preferably 25:75 to 95:5. Within this range, it is possible to ensure not only high refractive index but also a good color tone.

[Compound (B)]

The optical material composition may optionally comprise a compound (B). The compound (B) is an episulfide compound having two episulfide groups, which is represented by the following formula (2). The compound (B) is copolymerizable with the compound (A) and exerts the effect of increasing the curing reactivity of the composition when used together with the compound (A).

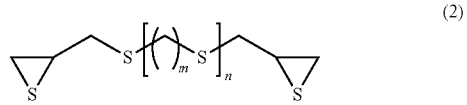

(2)

(wherein m represents an integer of 0 to 4, and n represents an integer of 0 to 2).

Above all, bis(β-epithiopropyl)sulfide and bis(β-epithiopropyl)disulfide are preferred, and bis(β-epithiopropyl)sulfide is particularly preferred. Bis(β-epithiopropyl)sulfide corresponds to a compound of the above formula (2) where m=n=0. Bis(β-epithiopropyl)disulfide corresponds to a compound of the above formula (2) where m=0 and n=1.

The content of the compound (B) in the optical material composition is 0% to 30% by mass, and more preferably 0% to 25% by mass, relative to the total mass of the composition. Within this range, it is possible to improve curing-reactivity while ensuring a good color tone.

The mass ratio of the compound (A) to the compound (B) (i.e., compound (A):compound (B)) is preferably 45:55 to 100:0, and more preferably 50:50 to 100:0. Within this range, it is possible to ensure not only high refractive index but also a good color tone.

[Sulfur]

The optical material composition may optionally comprise sulfur. Sulfur has the effect of improving the refractive index of the optical material (resin) obtained from the optical material composition of the present invention.

For use in the present invention, sulfur may be of any shape. Specific examples include micronized sulfur, colloidal sulfur, precipitated sulfur, crystalline sulfur, sublimed sulfur and the like. Among them, preferred is micronized sulfur composed of fine particles in terms of its dissolution rate.

For use in the present invention, sulfur preferably has a particle size (diameter) less than 10 mesh. If sulfur has a particle size greater than 10 mesh, sulfur is difficult to dissolve completely. The particle size of sulfur is more preferably smaller than 30 mesh, and most preferably smaller than 60 mesh.

For use in the present invention, sulfur has a purity of preferably 98% or higher, more preferably 99.0% or higher, even more preferably 99.5% or higher, and most preferably 99.9% or higher. If the purity of sulfur is 98% or higher, the color tone of the resulting optical material will be greatly improved when compared to cases where the purity of sulfur is less than 98%.

Sulfur satisfying the above requirements may be readily obtained as a commercially available product, which is preferred for use.

The ratio of sulfur in the optical material composition is 0% to 40% by mass (e.g., 1% to 40% by mass), preferably 0% to 30% by mass (e.g., 5% to 30% by mass or 10% to 30% by mass), more preferably 0% to 25% by mass (e.g., 5% to 25% by mass), and particularly preferably 0% to 20% by mass (e.g., 5% to 20% by mass), relative to the total mass of the composition. This is because, within this range, it is possible to ensure a good balance between the improving effect on refractive index and solubility.

A compositional example of a preferred optical material composition is as follows.

An optical material composition, which comprises:

| | |
|---|---|
| the compound (A) | 20% to 80% by mass (more preferably 20% to 50% by mass); |
| 1,2,3,5,6-pentathiepane (b) | 5% to 70% by mass (more preferably 5% to 50% by mass); |
| the compound (B) | 0% to 30% by mass (more preferably 0% to 25% by mass); |
| the polythiol (a) | 0% to 10% by mass (more preferably 0% to 5% by mass); and |
| sulfur | 0% to 25% by mass (more preferably 0% to 20% by mass) | relative to the total mass of the composition.

Another compositional example of a preferred optical material composition is as follows.

An optical material composition, which comprises:

| | |
|---|---|
| the compound (A) | 20% to 80% by mass (more preferably 20% to 50% by mass); |
| 1,2,3,5,6-pentathiepane (b) | 5% to 70% by mass (more preferably 5% to 50% by mass); |
| the compound (B) | 0% to 30% by mass (more preferably 0% to 25% by mass); |
| the polythiol (a) | 0% to 10% by mass (more preferably 0% to 5% by mass); |

| | |
|---|---|
| sulfur | 0% to 25% by mass (more preferably 0% to 20% by mass); |
| a polymerization catalyst | 0% to 10% by mass (more preferably 0.0001% to 10% by mass); and |
| a polymerization regulator | 0% to 5% by mass (more preferably 0.0001 to 5.0% by mass) | relative to the total mass of the composition.

[Other Components]

Moreover, the optical material composition of the present invention may further comprise an additional polymerizable compound which is copolymerizable with the compound (A).

Examples of an additional polymerizable compound include any episulfide compound other than the compound (A) and the compound (B), a vinyl compound, a methacrylic compound, an acrylic compound and an allyl compound.

The amount of such an additional polymerizable compound to be added is not limited in any way as long as the effect of the present invention is not impaired. For example, it is 0% to 30% by mass relative to the total mass of the composition.

In addition, with the aim of various improvements in performance including oxidation resistance, weather resistance, dye affinity, strength and refractive index, compounds capable of reacting with some or all of the compositional components used in the present invention (including a polymerized product obtainable upon pre-polymerization reaction of the compositional components) may be added as various performance improvers, followed by polymerization and curing.

Specific examples of such compounds capable of reacting with some or all of the compositional components include epoxy compounds, iso(thio)cyanates, carboxylic acids, carboxylic acid anhydrides, phenols, amines, vinyl compounds, allyl compounds, acrylic compounds, and methacrylic compounds. The amount of these compounds to be added is not limited in any way as long as the effect of the present invention is not impaired. For example, it is 0% to 10% by mass relative to the total mass of the composition.

Moreover, for polymerization and curing, the optical material composition may comprise a polymerization catalyst and/or a polymerization regulator.

In one embodiment, the optical material composition further comprises a polymerization catalyst.

Examples of such a polymerization catalyst include amines, phosphines, quaternary ammonium salts, quaternary phosphonium salts, tertiary sulfonium salts, secondary iodonium salts, mineral acids, Lewis acids, organic acids, silicic acids, tetrafluoroboric acids, peroxides, azo compounds, condensates between aldehydes and ammonia-based compounds, guanidines, thioureas, thiazoles, sulfenamides, thiurams, dithiocarbamate salts, xanthate salts, acidic phosphate esters and so on. Preferred are amines, phosphines, quaternary ammonium salts, and quaternary phosphonium salts. These polymerization catalysts may be used either alone or as a mixture of two or more of them.

The amount of the polymerization catalyst to be added is not limited in any way. For example, it is 0.0001% to 10% by mass relative to the total mass of the composition.

In one embodiment, the optical material composition further comprises a polymerization regulator.

Examples of such a polymerization regulator include halides of Group 13 to 16 elements in the long-form periodic table. Among them, preferred are halides of silicon, germanium, tin and antimony, and more preferred are chlorides of germanium, tin and antimony, each having an alkyl group(s). These polymerization regulators may be used either alone or as a mixture of two or more of them.

The amount of the polymerization regulator to be added is not limited in any way. For example, it is 0.0001% to 5.0% by mass relative to the total mass of the composition.

It is also possible to add any known additives such as an antioxidant, a bluing agent, a UV absorber, an odor eliminator, an adhesion improver and a mold release improver. The amount of these additives is not limited in any way as long as the effect of the present invention is not impaired. For example, it is 0% to 10% by mass relative to the total mass of the composition.

[Optical Material Composition]

The optical material composition of the present invention is prepared when the compound (A), 1,2,3,5,6-pentathiepane (b), and optionally the compound (B), the polythiol (a), sulfur, and other components are mixed into a homogeneous state.

[Curing of the Optical Material Composition]

The optical material composition may be injected into a mold or the like and polymerized therein to give an optical material. The polymerizable optical material composition is preferably subjected to degassing treatment before being injected into a mold, in terms of achieving high transparency in the resulting optical material.

At the time of injecting the optical material composition of the present invention, it is preferable to remove impurities by filtration, e.g., through a filter having a pore size of about 0.1 to 5 µm, in terms of improving the quality of the optical material of the present invention.

The optical material composition of the present invention may generally be polymerized (cured) under the following conditions.

The curing time is generally 1 to 100 hours, and the curing temperature is generally −10° C. to 140° C. Polymerization (curing) may be accomplished by holding at a given polymerization temperature for a given period of time, by increasing the temperature at a rate of 0.1° C. to 100° C./h, by decreasing the temperature at a rate of 0.1° C. to 100° C./h, or by any combination thereof. It should be noted that the curing time refers to the time required for polymerization and curing including the process of increasing or decreasing the temperature, i.e., the curing time includes not only the time required for holding at a given polymerization (curing) temperature, but also the time required for increasing or decreasing the temperature to the given polymerization (curing) temperature.

In addition, after completion of the curing, the resulting optical material may be annealed at a temperature of 50° C. to 150° C. for about 10 minutes to 5 hours, which is preferred for removing distortions from the optical material of the present invention. Further, the resulting optical material may optionally be subjected to surface treatment such as dyeing, hard coating, impact resistance coating, antireflection, antifogging treatment, etc.

As described above, an optical material can be produced by polymerizing and curing the above optical material composition. The present invention encompasses a process for producing an optical material, which comprises polymerizing and curing the above optical material composition.

In addition, optical materials obtained upon curing the above optical material composition (e.g., molded products; cured products; cured resins) also fall within the present invention.

As a result of comprising the compound (A) and 1,2,3,5,6-pentathiepane (b), the optical material composition of the present invention can achieve good heat resistance and can also reduce the influence of reduced heat resistance due to addition of other comonomers. Thus, the optical material composition can be blended with various comonomers and their amount to be blended can also be increased, which in turn enables the design of an optical material having a wide range of physical properties.

In particular, the optical material composition in one embodiment of the present invention can result in an optical material with good heat resistance and high refractive index.

The optical material cured from the optical material composition has a refractive index of preferably 1.70 or higher, more preferably 1.75 or higher, and particularly preferably 1.78 or higher. The refractive index may be measured with a refractometer and is expressed as a value measured at 25° C. for e-ray (wavelength: 546.1 nm).

As to the heat resistance of the optical material, the optical material shows no softening point when heated, or has a softening point of preferably 50° C. or higher, and more preferably 55° C. or higher. The softening point may be measured by TMA (thermo-mechanical analysis). A smaller peak value in DTMA, which is a temperature derivative curve of the TMA curve, is more preferred because heat-induced softening is less likely to occur, and the peak value in DTMA is preferably 2 μm/° C. or less.

The optical material of the present invention is useful for various applications, as exemplified by optical members, mechanical component materials, electric or electronic component materials, automobile component materials, civil engineering and construction materials, molding materials and so on, as well as materials for coating materials and adhesives, etc. Among them, preferred are optical materials, as exemplified by lenses (e.g., spectacle lenses, image pickup lenses for (digital) cameras, light beam condenser lenses, light diffusion lenses); optical applications such as transparent glasses and cover glasses (e.g., LED sealers, optical adhesives, light transmission bonding materials, optical fibers, prisms, filters, diffraction gratings, watch glasses, display device cover glasses); and display device applications such as display element substrates for LCDs, organic ELs, PDPs, etc., color filter substrates, touch panel substrates, information recording substrates, display backlights, light-guiding panels, display protection films, antireflection films, antifogging films and other coatings (coating films), etc. Among the above optical materials, particularly preferred are optical lenses, prisms, optical fibers, information recording substrates, filters and so on, with optical lenses being most preferred.

Optical lenses produced from the optical material composition of the present invention are very useful because they are excellent in stability, hue, transparency and other properties and therefore can be used in the fields of telescopes, binoculars, television projectors and others where expensive high refractive index glass lenses have been used conventionally. They are preferably used in the form of aspherical lenses, as needed.

EXAMPLES

The present invention will be further described in more detail by way of the following examples. However, embodiments to carry out the present invention can be modified as appropriate, as long as the effect of the present invention is provided.

Analysis and evaluation on optical materials were conducted as described below.

[Refractive Index of Optical Material]

The refractive index of an optical material was measured as a refractive index for e-ray at 25° C. with a digital high-precision refractometer (KPR-2000, a product of Shimadzu Corporation, Japan).

[Heat Resistance Evaluation on Optical Material]

A sample was cut into 3 mm thickness and subjected to TMA measurement (TMA/SS6100, a product of Seiko Instruments Inc., Japan) while applying a 50 g load to a pin of 0.5 mm diameter and increasing the temperature at a rate of 10° C./minute, followed by evaluation based on the peak temperature and the peak value in DTMA, which is a temperature derivative curve of the resulting TMA curve.

If this peak value is smaller, heat-induced softening is less likely to occur, and such a case is evaluated to be high in heat resistance. In particular, if the peak value is negative or if no peak is observed, such a case is evaluated to have no softening point.

Synthesis Example 1

Synthesis of tetrakis(β-epithiopropylthiomethyl)methane (Compound A1)

To tetramercaptopentaerythritol (10.0 g, 0.050 mol), methanol (50 mL) was added and cooled to 5° C. After addition of 48% aqueous sodium hydroxide (0.42 g, 0.0049 mol) to the resulting solution, epichlorohydrin (20.3 g, 0.22 mol) was added dropwise while keeping the solution at 15° C. or lower. After completion of the dropwise addition, the solution was further stirred for 1 hour at 5° C.

Then, a solution of 48% aqueous sodium hydroxide (16.3 g, 0.20 mol) in methanol (20 mL) was added dropwise while cooling the solution to 5° C. After completion of the dropwise addition, the solution was further stirred for 2 hours, and toluene (100 mL) and water (100 mL) were then added thereto. The toluene layer was washed three times with water and the solvent was distilled off to obtain tetrakis(β-epoxypropylthiomethyl)methane (20.1 g, 0.047 mol).

To the resulting tetrakis(β-epoxypropylthiomethyl)methane (20.1 g, 0.047 mol), toluene (100 mL), methanol (100 mL), acetic anhydride (1.24 g, 0.012 mol) and thiourea (30.5 g, 0.40 mol) were added and stirred at 20° C. for 24 hours. Then, toluene (400 mL) and 5% sulfuric acid (400 mL) was added, and the toluene layer was washed three times with water and the solvent was distilled off to obtain 16.8 g of tetrakis(β-epithiopropylthiomethyl)methane as a crude product. The crude product was further subjected to silica gel column purification to obtain 11.2 g (0.023 mol) of tetrakis(β-epithiopropylthiomethyl)methane (hereinafter referred to as compound A1).

Compound A1 used in the following experiments was synthesized in this way.

Example 1

65 parts by mass of tetrakis(β-epithiopropylthiomethyl)methane (compound A1) falling within the compound (A), 35 parts by mass of 1,2,3,5,6-pentathiepane (b) (hereinafter simply referred to as "pentathiepane (b)"), 0.02 parts by mass of tetra-n-butylphosphonium bromide serving as a polymerization catalyst, and 0.05 parts by mass of di-n- butyltin dichloride serving as a polymerization regulator were degassed under vacuum with mixing to obtain an optical material composition.

The resulting optical material composition was polymerized and cured by heating at 30° C. for 10 hours, heating up to 100° C. over 10 hours and finally heating at 100° C. for 5 hours. After cooling, the cured product was annealed at 120° C. for 30 minutes. The resulting optical material was evaluated and the results obtained are summarized in Table 1.

Examples 2 to 12 and Comparative Examples 1 to 4

In accordance with the composition indicated in Table 1, the same procedure as shown in Example 1 was repeated to obtain optical materials.

The resulting optical materials were evaluated and the results obtained are summarized in Table 1.

Moreover, in the case of further comprising a given amount of the compound (B) (Examples 5 to 12), it is confirmed that optical materials with high refractive index and good heat resistance are also obtained.

Particularly in Examples 8 to 12 where the compound (A), the compound (B), 1,2,3,5,6-pentathiepane (b), the polythiol (a) and sulfur were used in given amounts, it is confirmed that high refractive index above 1.79 and good heat resistance were able to be achieved.

On the other hand, Comparative Examples 1 to 3 free from the compound (A) and Comparative Example 4 where the content of the compound (B) is higher than 30% by mass are confirmed to show poor heat resistance.

INDUSTRIAL APPLICABILITY

A cured product obtained from the optical material composition of the present invention upon polymerization and curing is preferred for use in optical materials including

TABLE 1

| | Composition (% by mass) | | | | | | | | Evaluation on optical material | | |
| | | | | | | | | | | DTMA peak | |
| | Compound | Polythiol (a) | | Pentathiepane | | Compound (B) | | | Refractive | Temperature | Value |
| | (A) | Type | Content | (b) | Sulfur | Type | Content | (A):(B) | index | [° C.] | [μm/° C.] |
| Example 1 | 65 | — | 0 | 35 | 0 | — | 0 | — | 1.752 | 65 | 1.3 |
| Example 2 | 70 | a1 | 10 | 20 | 0 | — | 0 | — | 1.734 | No softening point | |
| Example 3 | 80 | a1 | 10 | 10 | 0 | — | 0 | — | 1.724 | No softening point | |
| Example 4 | 60 | a1 | 5 | 25 | 10 | — | 0 | — | 1.758 | 78 | 0.35 |
| Example 5 | 55 | — | 0 | 35 | 0 | B1 | 10 | 85:15 | 1.751 | 63 | 1.6 |
| Example 6 | 40 | a1 | 10 | 20 | 0 | B1 | 30 | 57:43 | 1.730 | 57 | 1.5 |
| Example 7 | 40 | a1 | 10 | 10 | 10 | B1 | 30 | 57:43 | 1.751 | 60 | 1.1 |
| Example 8 | 25 | a1 | 1 | 30 | 19 | B1 | 25 | 50:50 | 1.799 | No softening point | |
| Example 9 | 25 | a2 | 1 | 30 | 19 | B1 | 25 | 50:50 | 1.800 | No softening point | |
| Example 10 | 25 | a3 | 1 | 30 | 19 | B1 | 25 | 50:50 | 1.800 | No softening point | |
| Example 11 | 40 | a3 | 1 | 45 | 9 | B1 | 5 | 89:11 | 1.794 | No softening point | |
| Example 12 | 25 | a1 | 1 | 30 | 19 | B2 | 25 | 50:50 | 1.801 | No softening point | |
| Comparative Example 1 | 0 | — | 0 | 35 | 0 | B1 | 65 | — | 1.751 | 53 | 7.3 |
| Comparative Example 2 | 0 | a1 | 10 | 20 | 0 | B1 | 70 | — | 1.729 | 48 | 6 |
| Comparative Example 3 | 0 | a1 | 5 | 25 | 10 | B1 | 60 | — | 1.755 | 48 | 3.1 |
| Comparative Example 4 | 30 | a1 | 10 | 20 | 0 | B1 | 40 | 43:57 | 1.729 | 52 | 2.5 |

It should be noted that the numerical values in the table represent the amounts (parts by mass) of the compounds contained in each composition. Moreover, the symbols a1 to a3, B1 and B2 appearing in the table along with the numerical values represent the compounds used. The compounds used in the table are as follows.

A1: Tetrakis(β-epithiopropylthiomethyl)methane
a1: Bis(2-mercaptoethyl)sulfide
a2: 1,3-Bis(mercaptomethyl)benzene
a3: 1,2,6,7-Tetramercapto-4-thiaheptane
B1: Bis(β-epithiopropyl)sulfide
B2: Bis(β-epithiopropyl)disulfide It should be noted that the compound a3 may be synthesized, for example, by the process described in JP 2005-263791 A.

As can be seen from Table 1 above, in case of using optical material compositions each comprising the compound (A) represented by formula (1) and 1,2,3,5,6-pentathiepane (b), and optionally the polythiol (a) and sulfur (Examples 1 to 4), it is confirmed that optical materials with high refractive index and good heat resistance are obtained.

plastic lenses, prisms, optical fibers, information recording substrates, filters and adhesives.

The invention claimed is:

1. An optical material composition, which comprises a compound (A) represented by the following formula (1), 1,2,3,5,6-pentathiepane (b), and optionally a compound (B) represented by the following formula (2), wherein the content of the compound (B) is 0% to 30% by mass relative to the total mass of the composition, and wherein the content of 1,2,3,5,6-pentathiepane (b) is 5% to 70% by mass relative to the total mass of the composition:

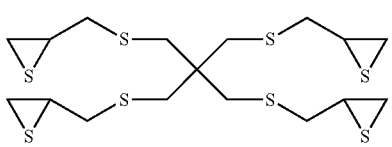

(1)

-continued

(2)

(wherein m represents an integer of 0 to 4, and n represents an integer of 0 to 2).

2. The optical material composition according to claim 1, wherein the content of the compound (A) is 20% to 80% by mass relative to the total mass of the composition.

3. The composition according to claim 1, which further comprises a polythiol (a).

4. The composition according to claim 3, wherein the polythiol (a) is at least one selected from 1,2,6,7-tetramercapto-4-thiaheptane, methanedithiol, (sulfanylmethyldisulfanyl)methanethiol, bis(2-mercaptoethyl)sulfide, 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, tetramercaptopentaerythritol, 1,3-bis(mercaptomethyl)benzene, 1,4-bis(mercaptomethyl)benzene, and thiiranemethanethiol.

5. The composition according to claim 1, which further comprises sulfur.

6. The composition according to claim 1, wherein the mass ratio of the compound (A) to the compound (B) is 45:55 to 100:0.

7. The composition according to claim 1, wherein the mass ratio of the compound (A) to 1,2,3,5,6-pentathiepane (b) is 25:75 to 95:5.

8. The composition according to claim 1, which comprises:

| the compound (A) | 20% to 80% by mass; |
| 1,2,3,5,6-pentathiepane (b) | 5% to 70% by mass; |
| the compound (B) | 0% to 30% by mass; |
| a polythiol (a) | 0% to 10% by mass; and |
| sulfur | 0% to 25% by mass | relative to the total mass of the composition.

9. The composition according to claim 1, wherein the composition when cured has a refractive index of 1.75 or higher for e-ray at 25° C.

10. An optical material cured from the composition according to claim 1.

11. An optical lens comprising the optical material according to claim 10.

12. An optical material composition, which comprises a compound (A) represented by the following formula (1), 1,2,3,5,6-pentathiepane (b), and optionally a compound (B) represented by the following formula (2),
wherein the mass ratio of the compound (A) to 1,2,3,5,6-pentathiepane (b) is 25:75 to 95:5, and
wherein the content of the compound (B) is 0% to 30% by mass relative to the total mass of the composition:

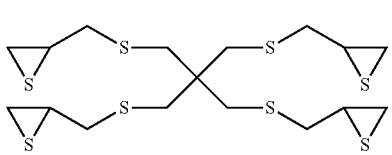
(1)

(2)

(wherein m represents an integer of 0 to 4, and n represents an integer of 0 to 2).

13. An optical material composition, which comprises a compound (A) represented by the following formula (1), 1,2,3,5,6-pentathiepane (b), and optionally a compound (B) represented by the following formula (2),
wherein the content of the compound (B) is 0% to 30% by mass relative to the total mass of the composition:

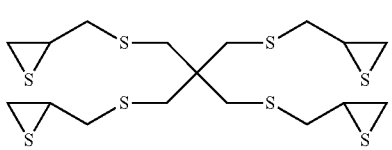
(1)

(2)

(wherein m represents an integer of 0 to 4, and n represents an integer of 0 to 2), which comprises:

| the compound (A) | 20% to 80% by mass; |
| 1,2,3,5,6-pentathiepane (b) | 5% to 70% by mass; |
| the compound (B) | 0% to 30% by mass; |
| the polythiol (a) | 0% to 10% by mass; and |
| sulfur | 0% to 25% by mass | relative to the total mass of the composition.

* * * * *